US012678623B2

(12) United States Patent
Patil et al.

(10) Patent No.: US 12,678,623 B2
(45) Date of Patent: Jul. 14, 2026

(54) SYSTEM AND METHOD TO SELECT AMONG TRAJECTORIES FOR THERAPEUTIC STIMULATION OF A TARGET VOLUME REGION WITHIN THE BRAIN

(71) Applicant: REGENTS OF THE UNIVERSITY OF MICHIGAN, Ann Arbor, MI (US)

(72) Inventors: Parag G. Patil, Ann Arbor, MI (US); Akshay Rao, Troy, MI (US); Asra Askari, Ann Arbor, MI (US); Charles W Lu, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 303 days.

(21) Appl. No.: 18/283,117

(22) PCT Filed: Mar. 7, 2022

(86) PCT No.: PCT/US2022/019132
§ 371 (c)(1),
(2) Date: Sep. 20, 2023

(87) PCT Pub. No.: WO2022/211976
PCT Pub. Date: Oct. 6, 2022

(65) Prior Publication Data
US 2024/0165408 A1 May 23, 2024

Related U.S. Application Data

(60) Provisional application No. 63/168,834, filed on Mar. 31, 2021.

(51) Int. Cl.
*A61N 1/36* (2006.01)
*A61B 5/374* (2021.01)
(Continued)

(52) U.S. Cl.
CPC ............ *A61N 1/3606* (2013.01); *A61B 5/374* (2021.01)

(58) Field of Classification Search
CPC ................ A61N 1/3606; A61N 1/0534; A61N 1/36067; A61N 1/36139; A61N 1/36075;
(Continued)

(56) References Cited

U.S. PATENT DOCUMENTS

2011/0040351 A1 * 2/2011 Butson ................... G16H 20/40
607/59
2014/0081127 A1 * 3/2014 Patil ...................... A61B 34/20
607/45
(Continued)

FOREIGN PATENT DOCUMENTS

WO WO-2015149170 A1 * 10/2015 ........... A61N 1/0534
WO WO-2020261282 A1 12/2020

OTHER PUBLICATIONS

Written Opinion for PCT/US2022/019132 dated Jun. 21, 2022.
(Continued)

*Primary Examiner* — Brian T Gedeon
(74) *Attorney, Agent, or Firm* — MARSHALL, GERSTEIN & BORUN LLP

(57) ABSTRACT

A system and method for selecting a trajectory within the brain for placement of a stimulation probe for deep brain stimulation (DBS) treatment of an individual afflicted with an illness, condition, or disorder. Electrophysiological data attained within the brain of the individual is utilized with clinically determined regions of stimulation (for example, volume of tissue activated (VTA)) of other similarly-afflicted individuals having a positive operative outcome to assign an objective score, independent of anatomical structure (for example, not constrained within the subthalamic nucleus (STN)) to facilitate selection among prospective
(Continued)

trajectories for placement of the stimulation probe during DBS.

20 Claims, 7 Drawing Sheets

(51) Int. Cl.
| | |
|---|---|
| *A61B 34/10* | (2016.01) |
| *A61N 1/05* | (2006.01) |
| *G16H 50/20* | (2018.01) |

(58) Field of Classification Search
CPC ............ A61N 1/36082; A61N 1/36089; A61N 1/38096; A61N 1/36135; A61N 1/36064; A61N 2034/104; A61N 2034/107
See application file for complete search history.

(56) References Cited

U.S. PATENT DOCUMENTS

| | | | |
|---|---|---|---|
| 2017/0189686 A1* | 7/2017 | Steinke | A61N 1/36146 |
| 2019/0069797 A1 | 3/2019 | Naor et al. | |
| 2019/0321106 A1 | 10/2019 | Bergman et al. | |
| 2020/0297228 A1* | 9/2020 | Crawford | A61B 5/24 |
| 2021/0085257 A1 | 3/2021 | Patil et al. | |

OTHER PUBLICATIONS

International Search Report for PCT/US2022/019132 dated Jun. 21, 2022.
Lu Charles W et al., "High Density Microelectrode Recording Predicts Span of Therapeutic Tissue Activation Volumes in Subthalamic Deep Brain Stimulation for Parkinson Disease", Brain Stimulation, Elsevier, Amsterdam, NL, vol. 13, No. 2, Dec. 4, 2019, pp. 412-419.

* cited by examiner

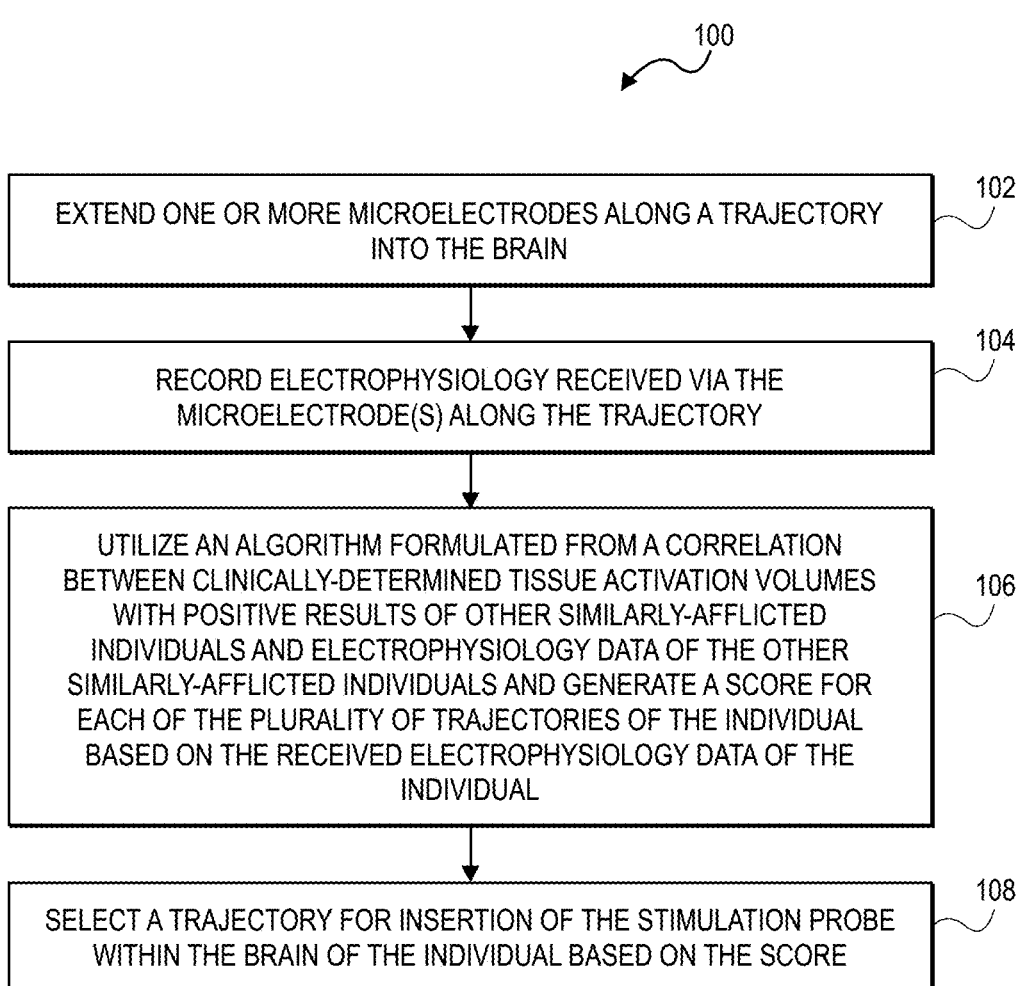

100

| | |
|---|---|
| EXTEND ONE OR MORE MICROELECTRODES ALONG A TRAJECTORY INTO THE BRAIN | 102 |
| RECORD ELECTROPHYSIOLOGY RECEIVED VIA THE MICROELECTRODE(S) ALONG THE TRAJECTORY | 104 |
| UTILIZE AN ALGORITHM FORMULATED FROM A CORRELATION BETWEEN CLINICALLY-DETERMINED TISSUE ACTIVATION VOLUMES WITH POSITIVE RESULTS OF OTHER SIMILARLY-AFFLICTED INDIVIDUALS AND ELECTROPHYSIOLOGY DATA OF THE OTHER SIMILARLY-AFFLICTED INDIVIDUALS AND GENERATE A SCORE FOR EACH OF THE PLURALITY OF TRAJECTORIES OF THE INDIVIDUAL BASED ON THE RECEIVED ELECTROPHYSIOLOGY DATA OF THE INDIVIDUAL | 106 |
| SELECT A TRAJECTORY FOR INSERTION OF THE STIMULATION PROBE WITHIN THE BRAIN OF THE INDIVIDUAL BASED ON THE SCORE | 108 |

FIG. 1

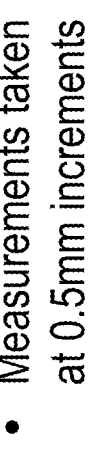
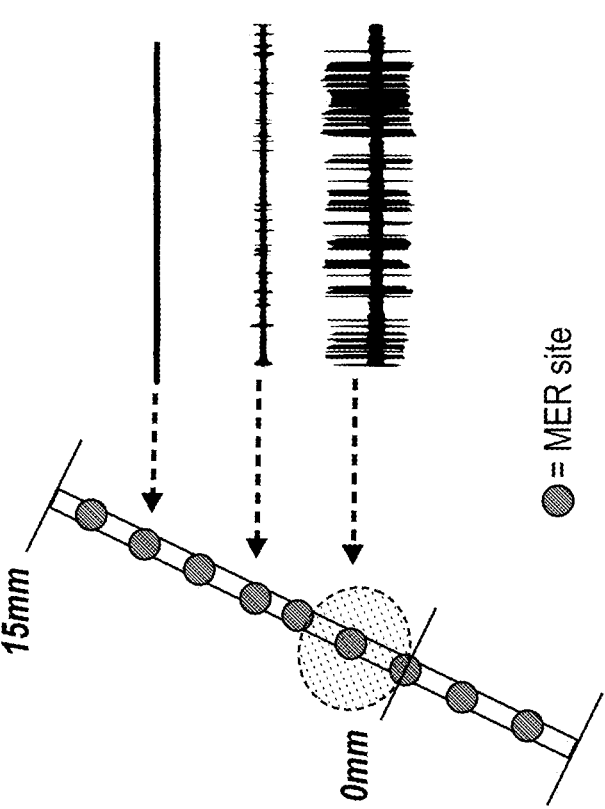
Methods: Microelectrode recordings
- Measurements taken at 0.5mm increments
- 15mm above target =>
  5mm below target
- Record for 6s/site
⬤ = MER site
15mm
0mm
FIG. 2

MER Features

LASSO-selected features: VTA vs. STN model

FIG. 3

Selection based on VTA score is predicted to improve clinical outcomes

Theoretical UPDRS % improvement: clinical vs. algorithm selection

If trajectories were selected purely based on MERcorrelated VTA score predictions, then among the incorrectly selected trajectories, there is a predicted 7.7 point improvement in overall UPDRS % improvement (p = 0.005348)

SYSTEM AND METHOD TO SELECT AMONG TRAJECTORIES FOR THERAPEUTIC STIMULATION OF A TARGET VOLUME REGION WITHIN THE BRAIN

CROSS-REFERENCE TO RELATED APPLICATIONS

This application is a national phase of PCT/US22/19132, filed Mar. 7, 2022, entitled: "System and Method to Select Among Trajectories for Therapeutic Stimulation of a Target Region Within the Brain" which claims priority to and the benefit of U.S. Provisional Application No. 63/168,834, filed on Mar. 31, 2021, entitled "System and Method to Select Among Trajectories for Therapeutic Stimulation of a Target Volume Region Within the Brain," the entire disclosures of which are hereby expressly incorporated by reference herein.

FIELD OF TECHNOLOGY

The following disclosure relates to therapeutic tissue stimulation for the treatment of an illness, condition, or disorder, and more particularly, to selecting among a plurality of trajectories for insertion of a stimulation probe within the brain.

RELATED APPLICATIONS

This application is related to pending U.S. patent application Ser. No. 16/582,734, "System and Method to Predict Target Volume Region For Therapeutic Tissue Activation," filed Sep. 25, 2019 (U.S. Publication No. 2021/0085257A1), attached hereto in the Appendix, the entire contents of which are expressly incorporated herein.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Deep brain stimulation (DBS) therapy is a known treatment for various human illnesses, conditions, and disorders (e.g., neurological), such as Parkinson's disease, Alzheimer's disease, essential tremor, dystonia, epilepsy, depression, and addiction. Successful DBS treatment relies on the effectiveness of the stimulation probe within the brain, which is dependent upon the location, i.e., trajectory path, of the probe and the specific resulting volume of tissue activated (VTA) along that path. For example, traditional selection of the trajectory path in the most common form of DBS for Parkinson's disease is generally constrained within the brain's subthalamic nucleus (STN) and determined by its span within. However, the STN structure does not capture all of the electrophysiological indicators of some illnesses, conditions, and disorders; in this example, Parkinson's disease. Consequently, a clear and unmet need exists for selecting an effective trajectory for the stimulation probe, independent of anatomic structures, for improved therapeutic stimulation treatment of the brain.

SUMMARY OF THE INVENTION

One embodiment of the invention described herein is a method for selecting a trajectory within the brain for insertion of a stimulation probe for deep brain stimulation treatment of an individual afflicted with a neurological illness, condition, or disorder. The method includes: extending one or more microelectrodes along a plurality of trajectories within the brain of the individual; receiving electrophysiology data at a plurality of increments along each of the plurality of trajectories, the electrophysiology data being indicative of neural activity of the individual; utilizing an algorithm including a correlation between clinically-determined tissue activation volumes with positive results of other similarly-afflicted individuals and electrophysiology data of the other similarly-afflicted individuals, to generate a score for each of the plurality of trajectories within the brain of the individual based on the received corresponding electrophysiology data of the individual; and, selecting a trajectory for insertion of the stimulation probe within the brain of the individual based on the score.

Another embodiment of the invention described herein is a system for selecting a trajectory within the brain for insertion of a stimulation probe for deep brain stimulation treatment of an individual afflicted with a neurological illness, condition, or disorder. The system includes: one or more processors; a user interface; one or more microelectrode probes; a stimulation probe; and a non-transitory computer-readable memory coupled to the one or more processors, the user interface, the one or more microelectrode probes, and the stimulation probe, wherein the non-transitory computer-readable memory including instructions stored thereon on that, when executed by the one or more processors, cause the system to: extend the one or more microelectrodes along a plurality of trajectories within the brain of the individual; receive electrophysiology data at a plurality of increments along each of the plurality of trajectories, the electrophysiology data being indicative of neural activity of the individual; utilize an algorithm including a correlation between clinically-determined tissue activation volumes with positive results of other similarly-afflicted individuals and electrophysiology data of the other similarly-afflicted individuals, to generate a score for each of the plurality of trajectories within the brain of the individual based on the received corresponding electrophysiology data of the individual; and, select a trajectory for insertion of the stimulation probe within the brain of the individual based on the score.

A further embodiment of the invention described herein is a non-transitory computer-readable memory operatively coupled to a deep brain stimulation system, the deep brain stimulation system including one or more processors operatively coupled to a user interface, one or more microelectrodes, and a stimulation probe, wherein the non-transitory computer-readable memory including instructions stored thereon on that, when executed by the one or more processors, cause the deep brain stimulation system to: extend the one or more microelectrodes along a plurality of trajectories within the brain of the individual; receive, via the one or more microelectrode probes, electrophysiology data at a plurality of increments along each of the plurality of trajectories, the electrophysiology data being indicative of neural activity of the individual; utilize an algorithm including a correlation between clinically-determined tissue activation volumes with positive results of other similarly-afflicted individuals and electrophysiology data of the other similarly-afflicted individuals, to generate a score for each of the plurality of trajectories of the individual based on the received corresponding electrophysiology data of the individual; and, select a trajectory for insertion of the stimulation probe within the brain of the individual based on the score.

BRIEF DESCRIPTION OF THE DRAWINGS

The figures described below depict various aspects of the systems and methods disclosed therein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 1 illustrates a flow diagram of an example method selecting a trajectory within the brain for insertion of a stimulation probe for deep brain stimulation treatment of an individual afflicted with a medical illness, condition, or disorder and performed in accordance with the embodiments described herein.

FIG. 2 is an enlarged image of one illustration of a prospective trajectory depicting a range of intervals for of microelectrode recordings (MER) in accordance with the embodiments described herein.

FIG. 3 depicts the coefficient strength of several MER covariate types that may be incorporated into the algorithm (e.g., MER-VTA model) for scoring prospective trajectories.

DETAILED DESCRIPTION

Figure 4:
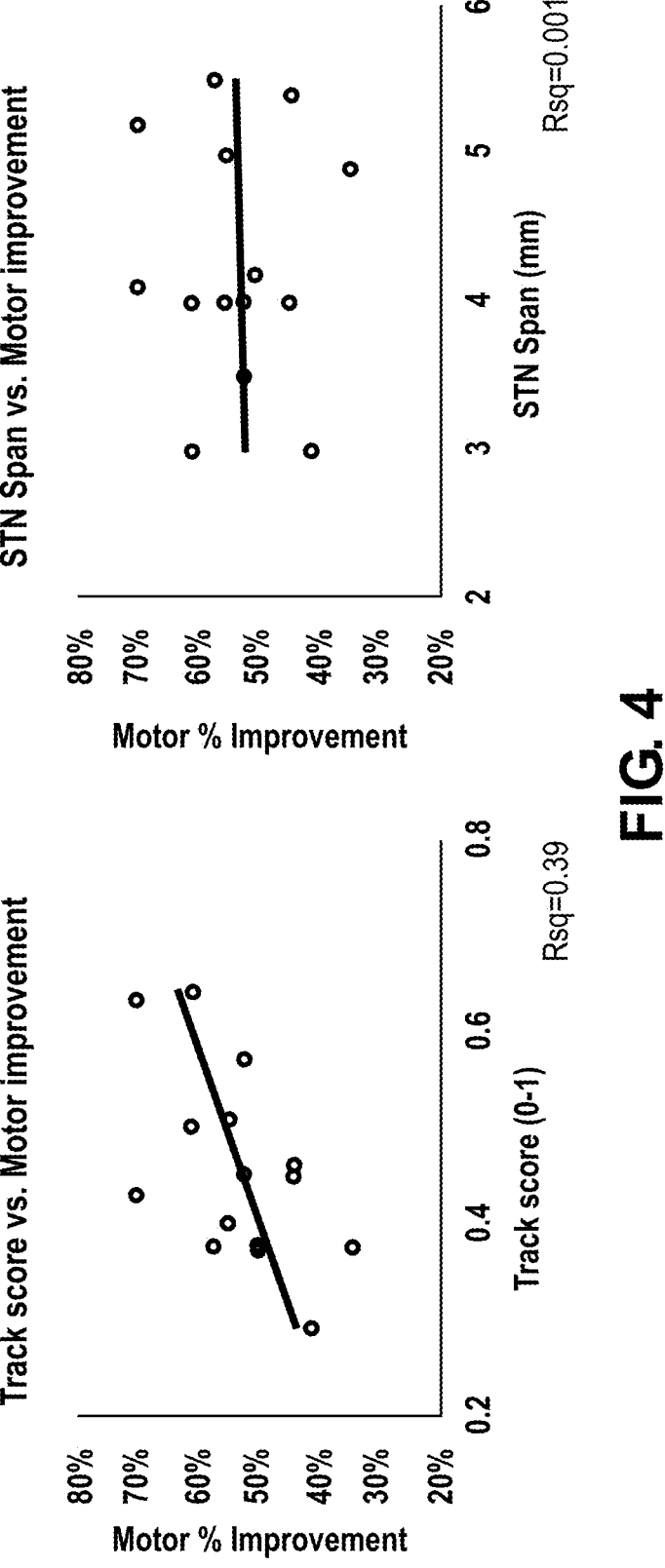
FIG. 4 is a graph depicting VTA activity strongly correlated (as compared to STN span) with UPDRS improvement.

Described herein are example systems and methods for selecting among a plurality of prospective trajectories (paths) within the brain for tissue stimulation or activation, which may facilitate a more effective therapeutic treatment for a variety of neurological-related illnesses, conditions, or disorders; such as brain tumors, hydrocephalus, movement disorders, Parkinson's disease, Alzheimer's disease, essential tremor, dystonia, epilepsy, depression, and addiction. In general, spatial data (e.g., location) of the volume(s) of tissue activated (VTA) in previous deep brain stimulation (DBS) procedures that yielded positive clinical outcomes (e.g., significant decrease in Unified Parkinson's Disease Rating Scale (UPDRS III)) are correlated with corresponding electrophysiological data (i.e., microelectrode recordings (MER)). The correlation is applied to future DBS procedures to select among prospective trajectories for an optimal site of stimulation (VTA) based on an individual's electrophysiological data (MER). The electrophysiological data may include of one or more processed electrophysiological parameters, e.g., traditionally defined frequency filters, which are utilized to determine a favorable trajectory among several prospective trajectories for stimulating the tissue activated volume (VTA). Utilizing electrophysiology data (MERs) correlated to VTAs with clinically determined positive results allows for an objective criterion, e.g., metric, score; for selecting among prospective trajectories that is independent of local anatomic structures, that is, stimulation along the trajectory path that is not limited to within the subthalamic nucleus (STN).

A flow diagram (100) of one implementation of an example method for selecting a trajectory within the brain for insertion of a stimulation probe for stimulation treatment, i.e., deep brain stimulation (DBS), of an individual afflicted with an illness and/or disorder is shown in FIG. 1. Initially, a data structure may be constructed of stimulation-treatment data of a plurality of other similarly-afflicted individuals. Composition of the data structure may include intraoperative electrophysiology data, e.g., neurological signals, stimulation parameters, etc., of the plurality of other treated individuals, which may be deduced from recorded electrophysiology activity (MER) received via a microelectrode traversing one or more trajectories within the brain of the plurality of other similarly-afflicted and treated individuals. The data structure includes an algorithm that correlates the microelectrode data to regions of stimulation within the brain (i.e., VTA) that have been clinically determined to have positive treatment results. Similarly, to attain electrophysiology data of the individual to be treated, a microelectrode is inserted into the brain along one or more trajectories (block 102).

The received electrophysiology data (block 104) includes normal neural activity of the individual, however it may also include neural activity in response to one or more stimuli, e.g., electrical, chemical, mechanical, and/or other sensory prompt, administered to the individual. Any attained electrophysiology data may be utilized with the algorithm to calculate and/or generate a score for a specific trajectory path within the brain based on the individual's electrophysiology data and its correlation to VTAs of prior DBS procedures that have clinically determined positive outcomes. The scores of several prospective trajectory paths that are candidates for insertion of a stimulation probe may be compared for selection (block 108). For example, the trajectory with the highest score may automatically be selected for insertion of the stimulation probe.

FIG. 2 is an enlarged image of one illustration (200) of a prospective trajectory (202) depicting example criteria for recording electrophysiology data of an individual. Microelectrode recordings (MER) are taken for 6 seconds at 0.5 mm increments from a range between 15 above a target, e.g., (subthalamic nucleus) and 5 mm below the target. The electrophysiology data may be recorded for multiple trajectories, for example, parallel tracks approximately 2 mm apart.

Figure 3:
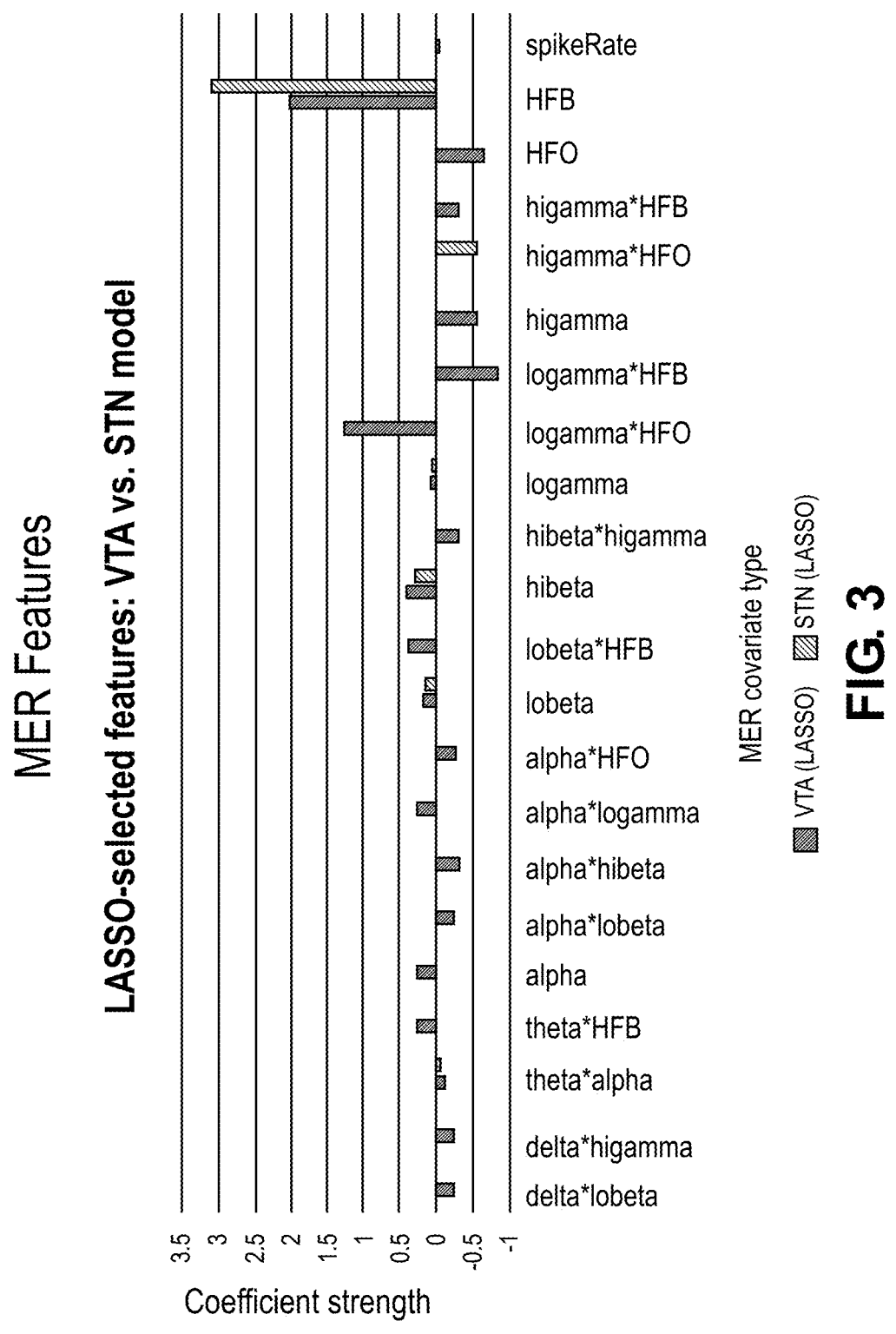

At each interval (i.e., depth), neurological-related activity, e.g., spike rate, log of normalized power; is calculated using various traditionally-defined frequency bands and/or ranges, e.g., delta (0.1-4 Hz), theta (4-8 Hz), alpha (8-13 Hz), beta (13-30 Hz), low gamma (30-59 Hz), high gamma (61-200 Hz), high-frequency oscillation (HFO; 200-400 Hz) and high-frequency band (HFB; 500-2000 Hz). Machine learning techniques, such as, but not limited to, prediction model, statistical analysis, support vector machine, and naïve Bayes; may be applied to the electrophysiology data to identify predictors associated with the clinically-validated therapeutic stimulation areas (VTAs). For example, a regression method such as logistic LASSO (least absolute shrinkage and selection operator) may be utilized to identify electrophysiology parameters, aspects, or features that provide a predictive value(s) for identifying tissue activation volumes (VTAs). Neural features, e.g., frequency, that may exhibit a predictive value include, but are not limited to: alpha, low beta, high beta, low gamma, high gamma, high-frequency oscillations (HFO), and high-frequency band (HFB) spike rate. Additionally, interactions of neural features (e.g., frequencies) that may also provide a predictive value, include, but are not limited to: delta interacting with low beta, delta interacting with high gamma, theta interacting with alpha, theta interacting with high-frequency band (HFB), alpha interacting with low beta, alpha interacting with high beta, alpha interacting with low gamma, alpha interacting with high-frequency oscillations (HFO), low beta interacting with high-frequency band (HFB), high beta interacting with high gamma, low gamma interacting with high-frequency oscillations (HFO); low gamma interacting with high-frequency band (HFB); high gamma interacting with high-frequency oscillations (HFO), and high gamma interacting with high-frequency band (HFB). FIG. 3 depicts the coefficient strength of several MER covariate types that may be incorporated into the algorithm (e.g., MER-VTA model) for scoring prospective trajectories in relation to stimulation region (VTA).

The algorithm calculates an objective score for each prospective trajectory based on the electrophysiology data of each trajectory. The recorded electrophysiology data (e.g., neural features) of the individual is input into the algorithm, which is correlated with regions of stimulation (VTA) of previous DBS procedures that have been clinically determined to have positive results, and calculates the score. For example, a probability of each increment of MER within a prospective trajectory may be calculated, wherein the score (e.g., between 0 and 1) represents the maximum probability along the trajectory, after the trajectory has been smoothed with a moving average filter. Each prospective trajectory may be compared to a threshold value and/or compared among all the candidate trajectories, wherein the trajectory with the highest score may automatically be selected for reception of the stimulation probe.

Neural activity within the VTA, which is independent of anatomical structure (e.g., not constrained within the subthalamic nucleus (STN)), is strongly correlated with improvements of clinical treatments as shown in the graph of VTA activity and UPDRS improvement depicted in FIG. 4. There is insignificant or little such correlation when the trajectory is constrained (e.g., confined by anatomical structure) within the STN.

Figure 5:
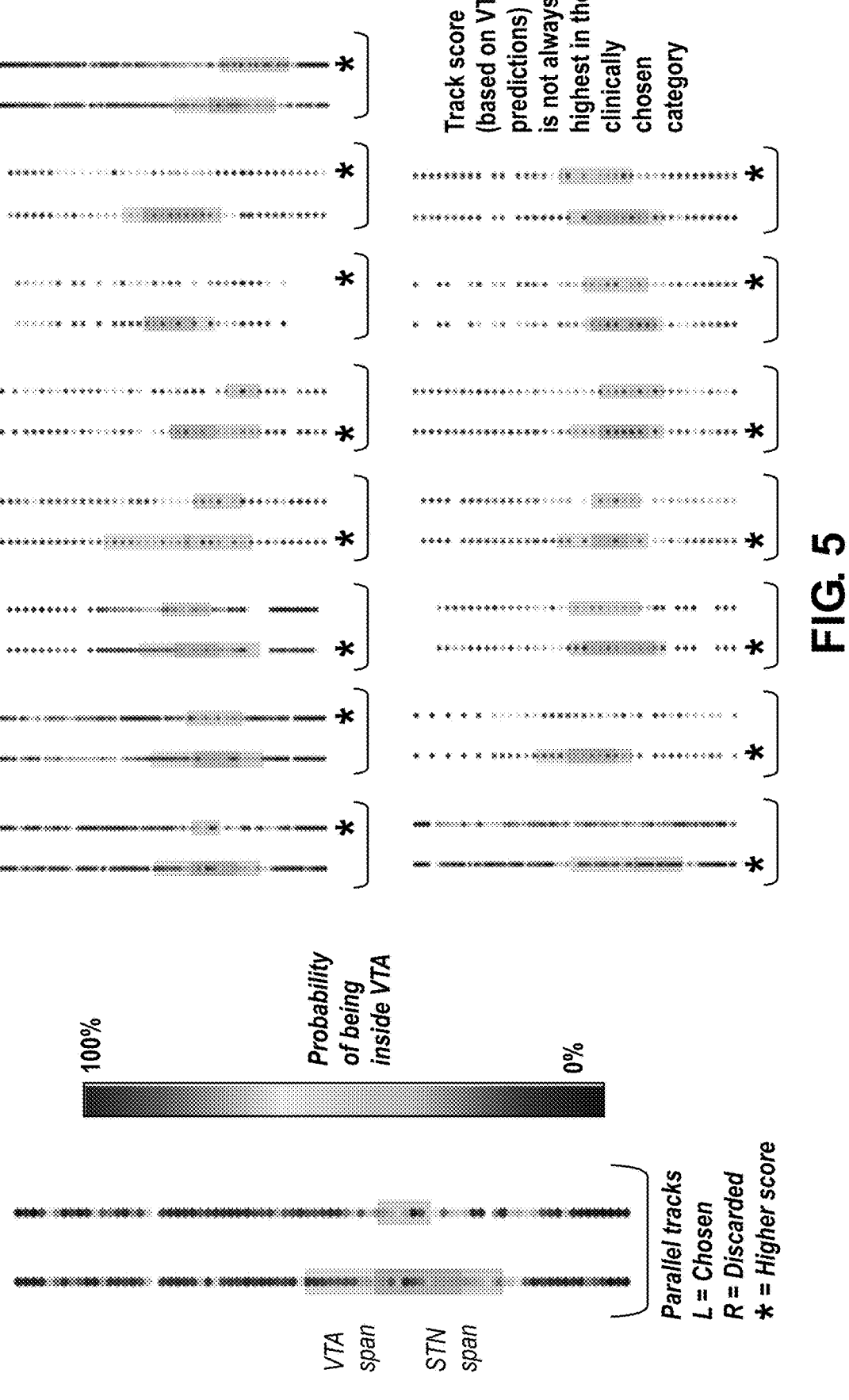
FIG. 5 is a graph depicting analysis of previous DBS surgeries where the trajectory selected for surgery did not exhibit the highest calculated VTA-correlated MER activity.
Figure 6:
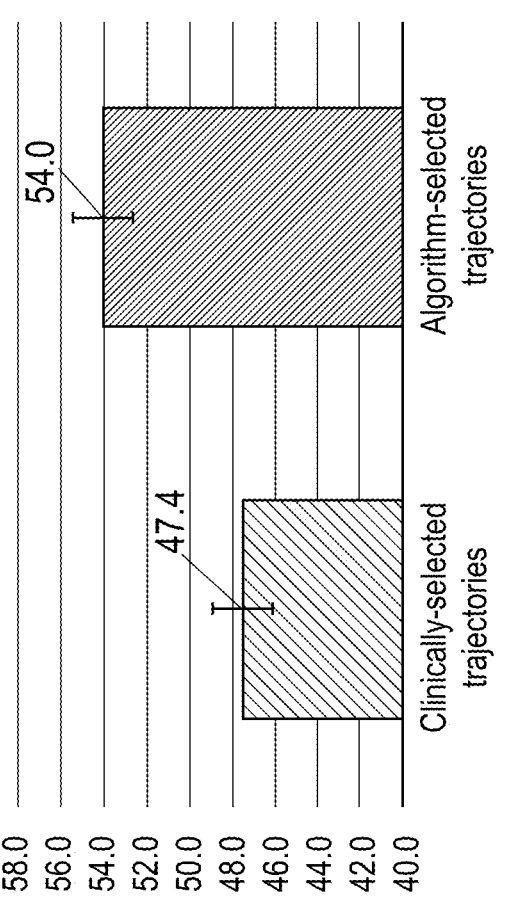
FIG. 6 is a chart depicting a proposed theoretical improvement in overall UPDRS % through selection of the prospective trajectory for DBS in accordance with the embodiments described herein as compared to traditional clinically selected trajectories.

FIG. 5 is a graph depicting analysis of previous DBS surgeries where the trajectory selected for surgery (presumably based on the current state-of-the-art where the trajectory is selected based on having the longest span within the STN) did not exhibit the highest calculated VTA-correlated MER activity. In approximately 47% of individuals (N=15), the non-selected trajectory displayed more VTA activity (area under probability curve) than the trajectory that was selected for surgery. It is proposed that if trajectories were selected based on the objective criteria discussed above (i.e., correlated microelectrode recordings and clinically determined VTAs with positive results), a 7.7 point improvement in clinical outcomes (e.g., overall UPDRS % improvement) may be attained (see FIG. 6).

Figure 7:
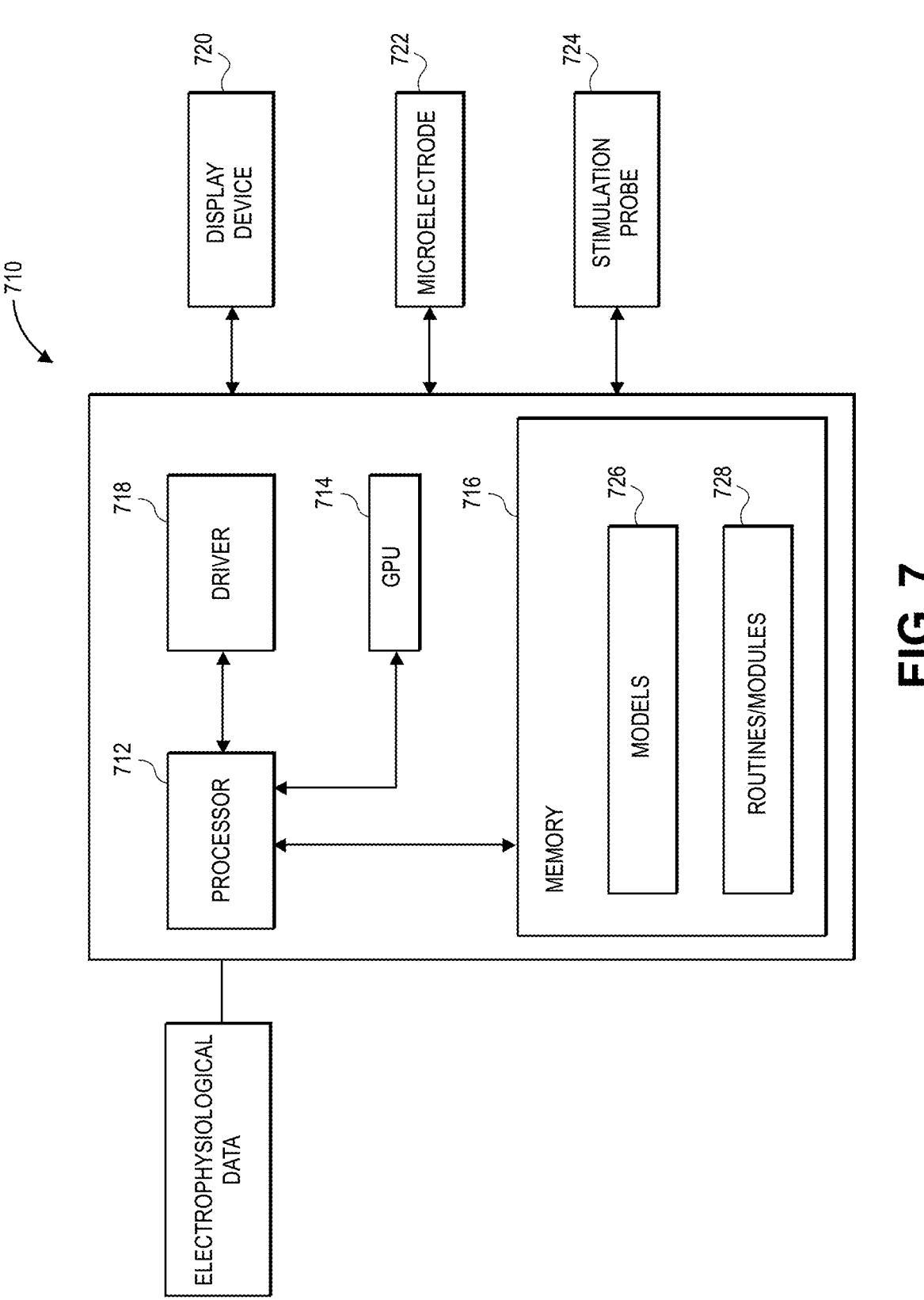
FIG. 7 illustrates an exemplary block diagram of an embodiment of a system assembled in accordance with the teachings of the present invention and used to facilitate selection of a trajectory within the brain of an individual for therapeutic stimulation.

FIG. 7 is a block diagram of one embodiment of a system 710 capable of executing the example methods described herein for selecting a trajectory for insertion of a stimulation probe within the brain of an individual based on an objective score that has been calculated from a correlation of the individual's microelectrode recordings (MER) and clinically determined VTAs of prior DBS procedures that had positive results. The system 710 includes one or more processors 712, one of which may be a graphical processor 714, any of which are operatively coupled to a memory 716 and a user interface, i.e., display device 720, for presenting stimulation information, such as images of the predicted tissue activation volume, trajectories within the brain, stimulation probe, microelectrode, etc. In some configurations, the display device 720 is a touchscreen and includes a software keyboard for entering text input, which may include stimulation parameters, patient information, etc. The display device can also include audio input and/or output components, such as a microphone and speaker, for example.

The system 710 further includes a stimulation probe 724 having at least one excitation area, and a microelectrode assembly 722 having at least on microelectrode probe, which are utilized by the one or more processors 712, 714, via a driver 718, to position either probe 722, 724 into the brain of the individual for detecting neural activity and/or stimulation treatment. In one example configuration, the microelectrode 722 includes a wideband low-noise amplifier, which may have differential amplifying capabilities, for example: a wideband range of 0 Hz to 10 kHz, and a signal gain per channel 1 to 100,000; a data acquisition card including 1 to 12 channel high impedance analog inputs, a digital converter to USB interface, and a variable sampling frequency between 1 Hz to 50 kHz. To facilitate low-noise recording and wideband signal analysis, the size and material properties of the microelectrode probe 722 may include a tip diameter between 40-100 μm or smaller, and an impedance between 1 kOhm and 1 MOhm or lower, for example. A shielded cable (not shown) may interface with the microelectrode 722 and an analog input to the amplifier to provide shielding against stray interference from other electronic hardware and to protect low amplitude raw signals received or captured by the microelectrode probe 722.

The processor 712 is capable of recording and processing electrophysiology data (MER), for example, neural activity, received by the microelectrode 722 (and/or stimulation probe with signal-receiving capabilities) and recording the data into the memory 716 and/or at a remote location. The memory 716 can be tangible, non-transitory memory and can include one or several suitable memory modules, such as random access memory (RAM), read-only memory (ROM), flash memory, other types of persistent memory, etc. The memory 716 may store stimulation parameters, training data, test data, etc., which may be configured into a data structure. The memory 716 may also store an operating system, which can be any type of suitable operating system, which can include application programming interface (API) functions that allow applications to retrieve sensor readings from the microelectrode assembly 722 and/or stimulation probe 724. For example, a software application (routine/module 720) configured to execute on the system 710 can include instructions that invoke an OS API to execute any portion of the machine learning prediction model, e.g., training the machine learning prediction model.

Models 726 and routines/modules 728, either of which may be in the form of a machine learning technique, a support vector machine, a naïve Bayes classifiers, etc., can be stored on the memory 716, wherein execution of any combination thereof by the processor 712 may perform at least one step in the stimulation treatment methods and machine learning techniques described above. For example, machine learning can be used to define the model/algorithm described herein to calculate the VTA score for each trajectory, but which may not be used during routine use. Some example machine learning models include, and are not limited to, the training, testing, predicting, analyzing, receiving, and stimulating methods described herein. Some example routines/modules include an imaging routine for illustrating stimulation treatment data for visual inspection, MRI imaging, etc.; an interface routine for facilitating interaction between a user and the neural targeting system; a probe implanting routine to facilitate execution of the driver 718 to implant the microelectrode probe 722 and the stimulation probe 724 into the brain of an individual to be treated; etc.

From the above, it is apparent that the integration of electrophysiology (MER) and spatial information of clinically determined positive results of a stimulated volume activated region (VTA), which may extend beyond the anatomical structure of the subthalamic nucleus (STN), can yield an identification of prospective trajectories within the brain (which are not constrained to within the STN) for a more effective DBS as compared to traditional methods that constrain the trajectory within the STN nucleus.

It should be understood that, unless a term is expressly defined in this patent using the sentence, "As used herein, the term '_____' is hereby defined to mean . . . ," or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

Furthermore, although the foregoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims. By way of example, and not limitation, the disclosure herein contemplates at least the following aspects.

Aspect 1. A method for selecting a trajectory within the brain for insertion of a stimulation probe for deep brain stimulation treatment of an individual afflicted with a neurological illness, condition, or disorder, the method comprising: extending, via the one or more processors, one or more microelectrodes along a plurality of trajectories within the brain of the individual; receiving, via the one or more microelectrodes, electrophysiology data at a plurality of increments along each of the plurality of trajectories, the electrophysiology data being indicative of neural activity of the individual; utilizing, via the one or more processors, an algorithm formulated with a correlation between clinically-determined tissue activation volumes with positive results of other similarly-afflicted individuals and electrophysiology data of the other similarly-afflicted individuals, to generate a score for each of the plurality of trajectories of the individual based on the received electrophysiology data of the individual; and selecting, via the one or more processors, a trajectory for insertion of the stimulation probe within the brain of the individual based on the score.

Aspect 2. The method of aspect 1, wherein parameters of the correlation include any of the following frequencies: alpha, low beta, high beta, low gamma, high gamma, high-frequency oscillations (HFO), and high-frequency band (HFB).

Aspect 3. The method of any combination of aspects 1 and 2, wherein parameters of the correlation include any of the following frequencies: delta interacting with low beta, delta interacting with high gamma, theta interacting with alpha, theta interacting with high-frequency band (HFB), alpha interacting with low beta, alpha interacting with high beta, alpha interacting with low gamma, alpha interacting with high-frequency oscillations (HFO), low beta interacting with high-frequency band (HFB), high beta interacting with high gamma, low gamma interacting with high-frequency oscillations (HFO); low gamma interacting with high-frequency band (HFB); high gamma interacting with high-frequency oscillations (HFO), and high gamma interacting with high-frequency band (HFB).

Aspect 4. The method of any combination of aspects 1-3, further comprising: implanting a stimulation probe along the selected trajectory within the brain of the individual; and activating the stimulation probe to stimulate the brain of the individual patient.

Aspect 5. The method of any combination of aspects 1-4, wherein activating the stimulation probe includes one or more activation contacts and/or one or more leads.

Aspect 6. The method of any combination of aspects 1-5, wherein the plurality of increments are spaced 0.5 mm apart along the trajectory and includes 6 seconds of microelectrode recording (MER).

Aspect 7. The method of any combination of aspects 1-6, wherein the microelectrode recordings are received within the range of 15 mm above a target and 5 mm below the target.

Aspect 8. The method of any combination of aspects 1-7, wherein the target is the subthalamic nucleus.

Aspect 9. The method of any combination of aspects 1-8, wherein the selecting a trajectory is based on a comparison of the score of the trajectory with a threshold and/or a comparison of the respective scores among the plurality of trajectories.

Aspect 10. A system for selecting a trajectory within the brain for insertion of a stimulation probe for deep brain stimulation treatment of an individual afflicted with a neurological illness, condition, or disorder, the system comprising: one or more processors; a user interface; one or more microelectrode probes; a stimulation probe; and a non-transitory computer-readable memory coupled to the one or more processors, the user interface, the one or more microelectrode probes, and the stimulation probe, wherein the non-transitory computer-readable memory including instructions stored thereon on that, when executed by the one or more processors, cause the system to: extend the one or more microelectrodes along a plurality of trajectories within the brain of the individual; receive, via the one or more microelectrode probes, electrophysiology data at a plurality of increments along each of the plurality of trajectories, the electrophysiology data being indicative of neural activity of the individual; utilize an algorithm formulated with a correlation between clinically-determined tissue activation volumes with positive results of other similarly-afflicted individuals and electrophysiology data of the other similarly-afflicted individuals, to generate a score for each of the plurality of trajectories of the individual based on the received corresponding electrophysiology data of the individual; and select a trajectory for insertion of the stimulation probe within the brain of the individual based on the score.

Aspect 11. The system of aspect 10, wherein the instructions further comprising: implant the stimulation probe along the selected stimulation trajectory within the brain of the individual; and activate the stimulation probe to stimulate the brain of the individual.

Aspect 12. The system of any combination of aspects 10 and 11, wherein the stimulation probe includes one or more activation contacts and/or one or more leads.

Aspect 13. The system of any combination of aspects 10-12, wherein parameters of the correlation include any of the following frequencies: alpha, low beta, high beta, low gamma, high gamma, high-frequency oscillations (HFO), and high-frequency band (HFB).

Aspect 14. The system of any combination of aspects 10-13, wherein parameters of the correlation include any of the following interactions of frequencies: delta interacting with low beta, delta interacting with high gamma, theta interacting with alpha, theta interacting with high-frequency band (HFB), alpha interacting with low beta, alpha interacting with high beta, alpha interacting with low gamma, alpha interacting with high-frequency oscillations (HFO), low beta interacting with high-frequency band (HFB), high beta interacting with high gamma, low gamma interacting with high-frequency oscillations (HFO); low gamma interacting with high-frequency band (HFB); high gamma interacting with high-frequency oscillations (HFO), and high gamma interacting with high-frequency band (HFB).

Aspect 15. The system of any combination of aspects 10-14, wherein the plurality of increments are spaced 0.5 mm apart along the trajectory and includes 6 seconds of microelectrode recording (MER).

Aspect 16. The system of any combination of aspects 10-15, wherein the microelectrode recordings are received within a range of 15 mm above a target and 5 mm below the target.

Aspect 17. The system of any combination of aspects 10-16, wherein the target is the subthalamic nucleus.

Aspect 18. The system of any combination of aspects 10-17, wherein the selection of a trajectory is based on a comparison of the score of the trajectory with a threshold and/or a comparison among the respective scores of the plurality of trajectories.

Aspect 19. A non-transitory computer-readable memory operatively coupled to a deep brain stimulation system, the deep brain stimulation system including one or more processors, a user interface, one or more microelectrodes, and a stimulation probe, wherein the non-transitory computer-readable memory including instructions stored thereon that, when executed by the one or more processors, cause the deep brain stimulation system to: extend the one or more microelectrodes along a plurality of trajectories within the brain of the individual; receive, via the one or more microelectrode probes, electrophysiology data at a plurality of increments along each of the plurality of trajectories, the electrophysiology data being indicative of neural activity of the individual; utilize an algorithm formulated with a correlation between clinically-determined tissue activation volumes with positive results of other similarly-afflicted individuals and electrophysiology data of the other similarly-afflicted individuals, to generate a score for each of the plurality of trajectories of the individual based on the received corresponding electrophysiology data of the individual; and select a trajectory for insertion of the stimulation probe within the brain of the individual based on the score.

Aspect 20. The non-transitory computer-readable memory of aspect 19, wherein the instructions further comprising: implant the stimulation probe along the selected stimulation trajectory within the brain of the individual; and activate the stimulation probe to stimulate the brain of the individual patient.

What is claimed is:

1. A method for selecting a trajectory within a brain for insertion of a stimulation probe for deep brain stimulation treatment of an individual afflicted with a neurological illness, condition, or disorder, the method comprising:
   extending, via one or more processors, one or more microelectrodes along a plurality of trajectories within the brain of the individual;
   receiving, via the one or more microelectrodes, electrophysiology data at a plurality of increments along each of the plurality of trajectories, the electrophysiology data being indicative of neural activity of the individual;
   utilizing, via the one or more processors, a machine learning model to generate a score for each of the plurality of trajectories of the individual based on the received electrophysiology data of the individual; and
   selecting, via the one or more processors, the trajectory for insertion of the stimulation probe within the brain of the individual based on a comparison of the score of the trajectory with a threshold and/or a comparison of the respective scores among the plurality of trajectories,
   wherein the machine learning model has been trained prior to utilization using a set of training data, the set of training data including (i) clinically determined tissue activation volumes with positive results of other similarly afflicted individuals and (ii) electrophysiology data of the other similarly afflicted individuals.

2. The method of claim 1, wherein parameters of the set of training data include any of the following frequencies: alpha, low beta, high beta, low gamma, high gamma, high-frequency oscillations (HFO), or high-frequency band (HFB).

3. The method of claim 1, wherein parameters of the set of training data include any of the following frequencies: delta interacting with low beta, delta interacting with high gamma, theta interacting with alpha, theta interacting with high-frequency band (HFB), alpha interacting with low beta, alpha interacting with high beta, alpha interacting with low gamma, alpha interacting with high-frequency oscillations (HFO), low beta interacting with high-frequency band (HFB), high beta interacting with high gamma, low gamma interacting with high-frequency oscillations (HFO); low gamma interacting with high-frequency band (HFB); high gamma interacting with high-frequency oscillations (HFO), or high gamma interacting with high-frequency band (HFB).

4. The method of claim 1, further comprising:
   implanting a stimulation probe along the selected trajectory within the brain of the individual; and
   activating the stimulation probe to stimulate the brain of the individual patient.

5. The method of claim 4, wherein activating the stimulation probe includes one or more activation contacts and/or one or more leads.

6. The method of claim 1, wherein the plurality of increments are spaced 0.5 mm apart along the trajectory and includes 6 seconds of microelectrode recording (MER).

7. The method of claim 6, wherein the microelectrode recordings are received within a range between 15 mm above a target and 5 mm below the target.

8. The method of claim 7, wherein the target is the subthalamic nucleus of the brain.

9. The method of claim 1, wherein selecting the trajectory is based on a comparison of the score of the trajectory with a threshold and/or a comparison of the respective scores among the plurality of trajectories.

10. A system for selecting a trajectory within a brain for insertion of a stimulation probe for deep brain stimulation treatment of an individual afflicted with a neurological illness, condition, or disorder, the system comprising:

one or more processors;

a user interface;

one or more microelectrodes;

a stimulation probe; and a non-transitory computer-readable memory coupled to the one or more processors, the user interface, the one or more microelectrodes, and the stimulation probe, wherein the non-transitory computer-readable memory including instructions stored thereon on that, when executed by the one or more processors, cause the system to:

extend the one or more microelectrodes along a plurality of trajectories within the brain of the individual;

receive, via the one or more microelectrodes, electrophysiology data at a plurality of increments along each of the plurality of trajectories, the electrophysiology data being indicative of neural activity of the individual;

utilize a machine learning model to generate a score for each of the plurality of trajectories of the individual based on the received corresponding electrophysiology data of the individual; and select the trajectory for insertion of the stimulation probe within the brain of the individual based on a comparison of the score of the trajectory with a threshold and/or a comparison of the respective scores among the plurality of trajectories, wherein the machine learning model has been trained prior to utilization using a set of training data, the set of training data including (i) clinically determined tissue activation volumes with positive results of other similarly afflicted individuals and (ii) electrophysiology data of the other similarly afflicted individuals.

11. The system of claim 10, wherein the instructions further cause the system to:

implant the stimulation probe along the selected stimulation trajectory within the brain of the individual; and activate the stimulation probe to stimulate the brain of the individual.

12. The system of claim 11, wherein the stimulation probe includes one or more activation contacts and/or one or more leads.

13. The system of claim 10, wherein parameters of the set of training data include any of the following frequencies: alpha, low beta, high beta, low gamma, high gamma, high-frequency oscillations (HFO), or high-frequency band (HFB) spike rate.

14. The system of claim 10, wherein parameters of the set of training data include any of the following interactions of frequencies: delta interacting with low beta, delta interacting with high gamma, theta interacting with alpha, theta interacting with high-frequency band (HFB), alpha interacting with low beta, alpha interacting with high beta, alpha interacting with low gamma, alpha interacting with high-frequency oscillations (HFO), low beta interacting with high-frequency band (HFB), high beta interacting with high gamma, low gamma interacting with high-frequency oscillations (HFO); low gamma interacting with high-frequency band (HFB); high gamma interacting with high-frequency oscillations (HFO), or high gamma interacting with high-frequency band (HFB).

15. The system of claim 10, wherein the plurality of increments are spaced 0.5 mm apart along the trajectory and includes 6 seconds of microelectrode recording (MER).

16. The system of claim 15, wherein the microelectrode recordings are received within a range between 15 mm above a target and 5 mm below the target.

17. The system of claim 16, wherein the target is the subthalamic nucleus of the brain.

18. The system of claim 10, wherein the instructions that cause the system to select the trajectory cause the system to select the trajectory based on a comparison of the score of the trajectory with a threshold and/or a comparison among the respective scores of the plurality of trajectories.

19. A non-transitory computer-readable memory operatively coupled to a deep brain stimulation system, the deep brain stimulation system including one or more processors, a user interface, one or more microelectrodes, and a stimulation probe, wherein the non-transitory computer-readable memory including instructions stored thereon on that, when executed by the one or more processors, cause the deep brain stimulation system to:

extend the one or more microelectrodes along a plurality of trajectories within a brain of an individual;

receive, via the one or more microelectrodes, electrophysiology data at a plurality of increments along each of the plurality of trajectories, the electrophysiology data being indicative of neural activity of the individual;

utilize a machine learning model to generate a score for each of the plurality of trajectories of the individual based on the received corresponding electrophysiology data of the individual; and select a trajectory for insertion of the stimulation probe within the brain of the individual based on a comparison of the score of the trajectory with a threshold and/or a comparison of the respective scores among the plurality of trajectories, wherein the machine learning model has been trained prior to utilization using a set of training data, the set of training data including (i) clinically determined tissue activation volumes with positive results of other similarly afflicted individuals and (ii) electrophysiology data of the other similarly afflicted individuals.

20. The non-transitory computer-readable memory of claim 19, wherein the instructions further cause the deep brain stimulation system to:

implant the stimulation probe along the selected stimulation trajectory within the brain of the individual; and activate the stimulation probe to stimulate the brain of the individual patient.

* * * * *